(12) United States Patent
Anderson (10) Patent No.: US 6,264,901 B1
(45) Date of Patent: Jul. 24, 2001

(54) SPACE FRAME STERILIZER DOOR (75) Inventor: Gary L. Anderson, Erie, PA (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/185,186

(22) Filed: Nov. 3, 1998

(51) Int. Cl.[7] .................................. A61L 2/00; A61L 2/07
(52) U.S. Cl. .............................. 422/295; 49/501; 49/504; 422/40; 422/276; 422/277; 422/295
(58) Field of Search ....................... 49/501, 503; 222/201, 222/40, 55, 276, 277, 278; 422/295

(56) References Cited

U.S. PATENT DOCUMENTS

| | | | |
|---|---|---|---|
| 4,590,710 | * 5/1986 | Newland | 49/478 |
| 5,146,713 | 9/1992 | Grafius . | |
| 5,195,790 | 3/1993 | Bulko et al. . | |
| 5,237,777 | 8/1993 | Houston et al. . | |
| 5,249,392 | * 10/1993 | Houston et al. | 49/360 |
| 5,386,674 | * 2/1995 | Sfirakis et al. | 49/503 |
| 5,566,508 | 10/1996 | Houston . | |
| 6,017,105 | * 1/2000 | Goughnour et al. | 49/209 |

* cited by examiner

Primary Examiner—Robert J. Warden, Sr.
Assistant Examiner—Imad Soubra
(74) Attorney, Agent, or Firm—Fay, Sharpe, Fagan, Minnich & McKee, LLP (57) ABSTRACT A door (18) for sealing the opening (14) to a walk-in steam sterilizer is formed from a stainless steel plate (50), sized to cover the opening, and a load-bearing framework (52), which is formed from a material having a different coefficient of thermal expansion to that of the plate, such as carbon steel. The framework includes a set of horizontally-spaced I beams (60) which are connected together at their ends by an outer frame (64). The framework is flexibly connected to an exterior surface of the plate by a number of flexible joints (56), such as carbon steel straps. The straps are welded at either end to the plate to form loops. The I beams are supported in the loops. As the temperature inside the sterilizer changes, causing the components of the door to expand or contract, the framework and the plate are able to expand or contract at different rates without resulting in bowing or other distortion of the door. Sets of rollers (22, 24) are rotatably mounted to upper and lower ends of the outer frame. The rollers engage upper and lower tracks (30, 36) mounted to the exterior of the sterilizer for sliding the door into and out of the closed position. In the closed position, flanges (82, 84, 86, 88) on the outer frame engage stopping plates (30, 36, 40, 90) on the exterior (16) of the sterilizer to hold the door in position across the opening. An active seal (94) is activated to seal the plate to the exterior of the sterilizer.

21 Claims, 8 Drawing Sheets

SPACE FRAME STERILIZER DOOR

BACKGROUND OF THE INVENTION

The present invention relates to the sterilization arts. It finds particular application in connection with a sliding sterilizer door for sealing the opening to a sterilization chamber, and will be described with particular reference thereto. It should be appreciated, however, that the invention is also applicable to a variety of doors which are subject to thermal and mechanical stresses during their operation.

Steam sterilizers generally operate over a range of internal temperatures and pressures. The temperature and pressure within the sterilizer are varied as the sterilization cycle progresses. To withstand the fluctuating pressures, sterilizer doors are generally constructed from a solid metal plate. For additional strength, a supporting structure may be welded to an exterior surface of the plate.

For economic reasons, it is desirable for the door plate and the supporting structure to be formed from different materials. The doorplate is generally formed from a material which is both relatively strong and resistant to the chemical conditions of the sterilizer, such as stainless steel. The supporting structure may be formed from a material chosen solely for its strength as it need not be resistant to chemical degradation. The different materials used for the plate and the supporting structure frequently have different coefficients of expansion.

The temperature gradients in the sterilizer cause thermomechanical stresses to develop in the door. When heated, the different materials of the door expand to different extents. For larger doors, such as those used in walk-in steam sterilizers, such relative expansions are magnified, and tend to cause distortion of the door. The thermal distortion can hinder door operation during opening and closing and lower the service life of the door through fatigue of the materials.

One way to overcome the problem in larger doors is to use similar materials for both the door plate and supporting structure. However, this prevents use of the most economical mix of materials for construction of the door.

The present invention provides for a new and improved sterilizer door which overcomes the above-referenced problems and others.

SUMMARY OF THE INVENTION

In accordance with one aspect of the present invention, a walk-in steam microbial decontamination apparatus is provided. The apparatus includes a chamber for receiving items to be microbially decontaminated. The chamber has an opening. A door selectively seals the opening. The door includes a plate sized to cover the opening, a framework for providing the door with structural strength, and a floating connection which connects the framework to an exterior surface of the plate such that the framework and the plate are free to expand and contract separately in response to a change in temperature.

In accordance with another aspect of the present invention, a door for a sterilizer is provided. The door includes a plate sized to cover an opening in the sterilizer, a framework for providing the door with structural strength, and a floating connection which connects the framework to an exterior surface of the plate such that the framework and the plate are free to expand and contract separately in response to a change in temperature.

In accordance with yet another aspect of the present invention, a method for selectively sealing an opening in a steam cabinet is provided. The method includes connecting a framework to an exterior surface of a plate with floating connections such that the framework and the plate are free to expand and contract independently in response to changes in temperature, the plate being sized to seal the opening. The method further includes sealing an interior surface of the plate to the cabinet around the opening and selectively holding the framework adjacent an exterior surface of the plate to prevent the plate from buckling outward in response to steam pressure in the cabinet.

One advantage of the present invention is that it prevents thermal distortion of the door.

Another advantage of the present invention is that the door plate and the support structure may be made of different materials having different coefficients of thermal expansion.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
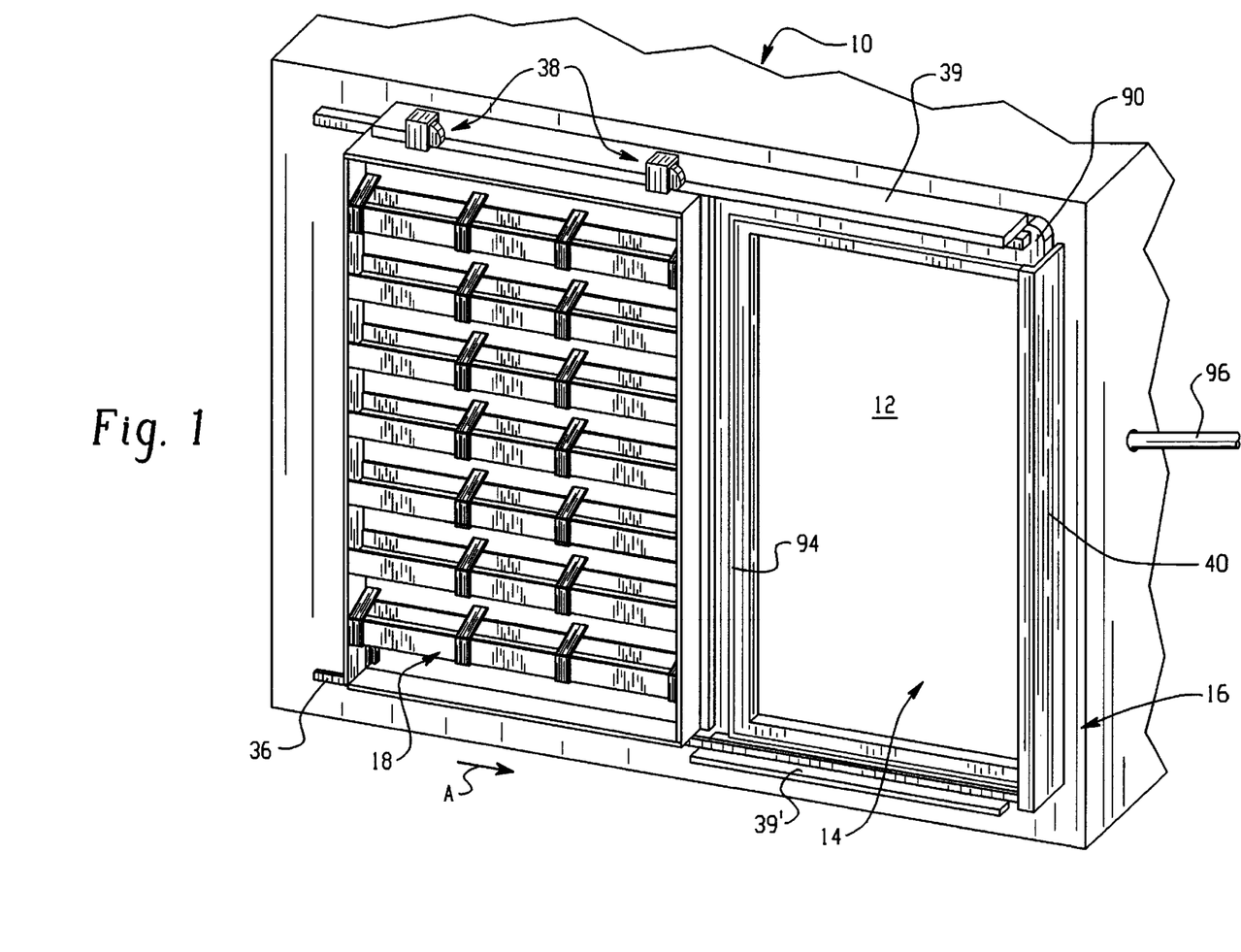
FIG. 1 is a front perspective view of a sterilizer with a space frame door, with its outer cover removed, in an open position and an overhead suspension system, according to the present invention.
Figure 2:
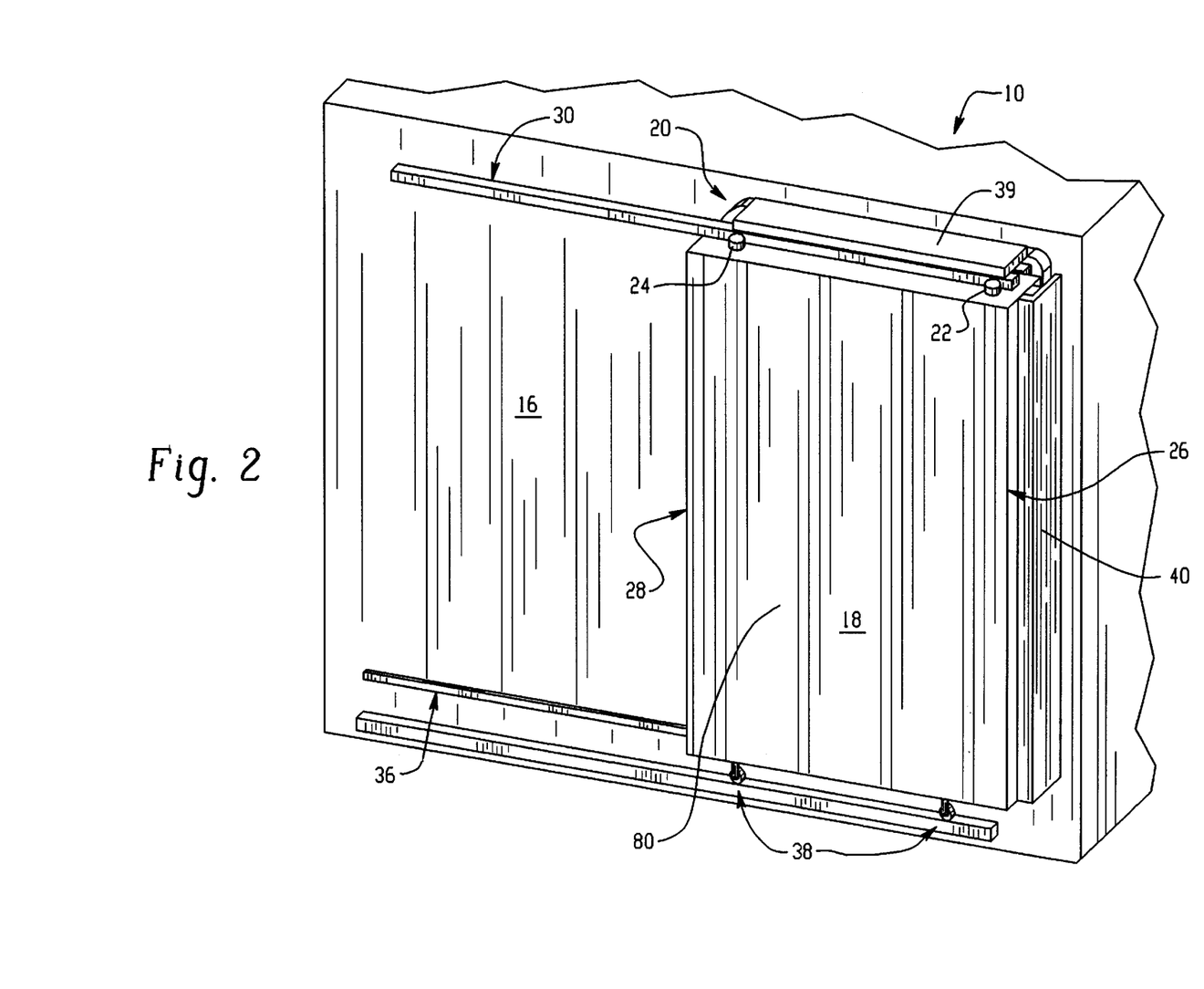
FIG. 2 is a front perspective view of another embodiment of a sterilizer with a space frame door in an closed position and a lower suspension system, according to the present invention.

With reference to FIGS. 1 and 2, a walk-in steam sterilizer includes a cabinet 10 which defines an interior chamber 12. Items to be sterilized are loaded into the chamber through an opening 14 which is defined in a front face 16 of the cabinet. A horizontal-sliding door 18, approximately 2–3 meters in height and 1–2 meters in width, selectively seals the opening.

Figure 3:
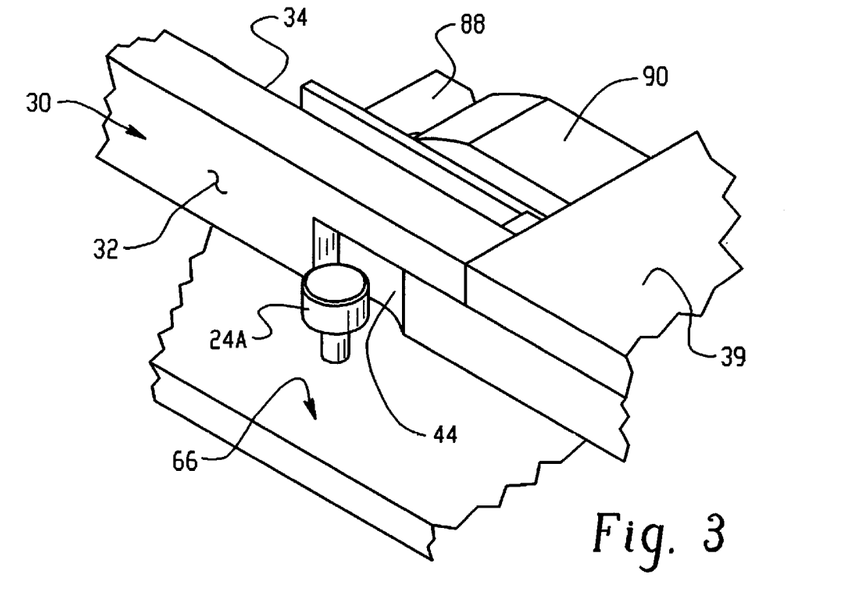
FIG. 3 is an enlarged perspective view of the trailing edge of the door of either of FIGS. 1 and 2 in the closed position.

With reference also to FIGS. 2 and 3, a door guidance system 20 guides the door during opening and closing. The door guidance system includes two pairs of upper rollers, namely a leading pair of rollers 22 and a trailing pair of rollers 24 which both extend upwardly from the door. The leading upper rollers 22 are positioned adjacent a leading vertical edge 26 of the door while the trailing rollers 24 are positioned adjacent a trailing vertical edge 28 of the door. The rollers slidingly engage an upper track 30 which extends horizontally adjacent to the front face 16 of the sterilizer above the opening 14.

Figure 4:
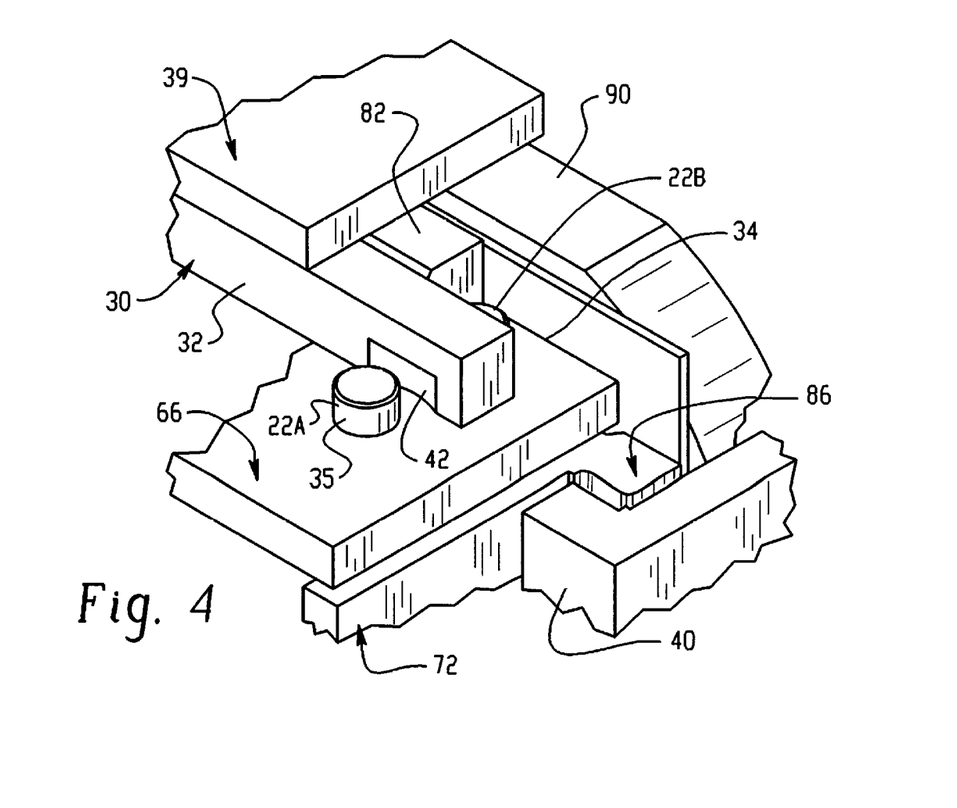
FIG. 4 is an enlarged perspective view of the leading edge of the door of either of FIGS. 1 and 2 in the closed position.

With reference also to FIGS. 3 and 4, outer rollers of each pair 22A and 24A, respectively, positioned furthest from the chamber, engage an outer vertical surface 32 of the track, while inner rollers 22B and 24B, positioned closest to the chamber, engage an inner vertical surface 34 of the track. Specifically, each of the rollers has a cylindrical peripheral face 35 which rolls along the corresponding vertical surface 32, 34 of the track. Similar lower rollers (not shown) engage outer and inner surfaces of a lower track 36. The rollers cooperate with the tracks 30, 36 to ensure that the door 18 is slightly spaced from the front face 16 of the sterilizer during opening and closing to avoid damage due to abrasion.

The weight of the door is carried by a suspension system 38. The suspension assembly may be an overhead system, as shown in FIG. 1, which carries the weight of the door from above, or a lower suspension system, as shown in FIG. 2, where the suspension assembly supports the door from below. The overhead suspension assembly is preferred because there is less likelihood of dirt becoming trapped in the assembly and thereby preventing smooth operation of the door.

A bracket 39 supports the upper track 30 from above. Specifically, the bracket extends outwardly from the front face 16 of the sterilizer over at least the part of the track which is adjacent to the opening 14. The track is connected to a lower surface of the bracket. A similar bracket 39' supports the lower track 36 from below.

To close the door, the door is pushed in a horizontal direction from an open position, as indicated by arrow A. The doors shown in FIGS. 1 and 2 are left-to-right sliding doors. It should be understood, however, that the doors could equally well close from right to left. The pairs rollers 22 and 24 guide the door along the tracks 30 and 36 until the leading edge of the door 26 engages a vertical stopping member or plate 40 which extends outwardly from the front face 16 of the sterilizer. When the leading edge engages the stopping member, the outer rollers 22A and 24A are disposed adjacent corresponding recesses 42 and 44 defined in the vertical surface 32 of the upper track. The lower rollers are disposed adjacent similar recesses defined in the lower track. Similar recesses may also be defined in the inner vertical face 34 adjacent to the upper inner rollers 22B and 24B, and in the corresponding inner vertical face of the lower track 36 for the lower inner rollers.

Figure 5:
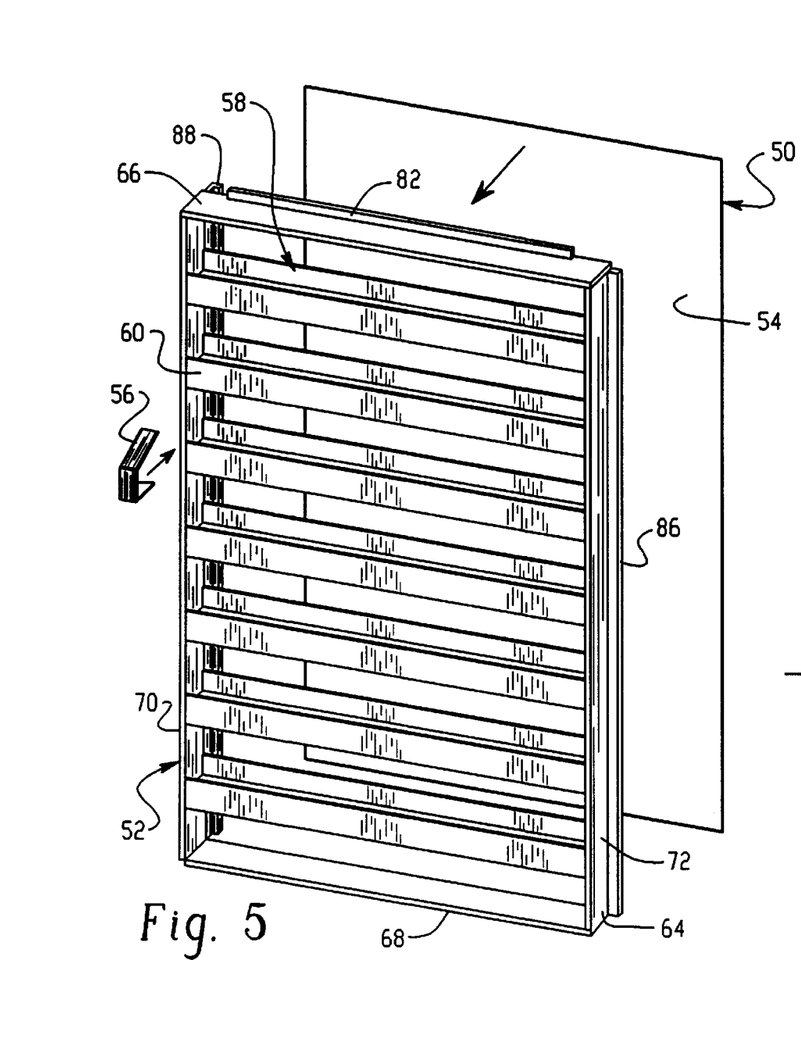
FIG. 5 is an exploded perspective view of the door of either of FIGS. 1 and 2.
Figure 6:
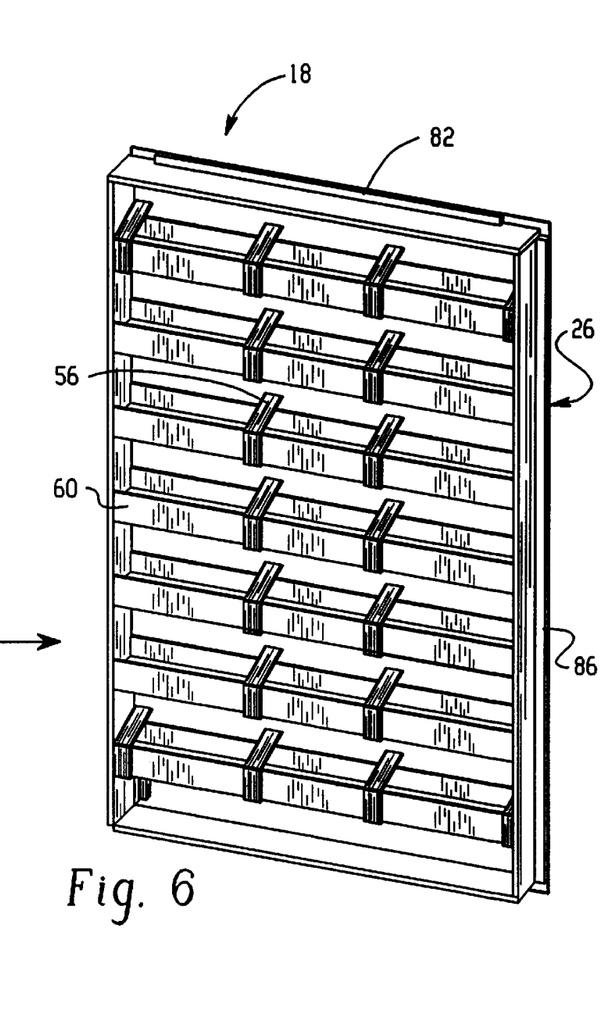
FIG. 6 is a perspective view of the door of either of FIGS. 1 and 2.

With reference to FIGS. 5 and 6, the door 18 includes a pressure-withstanding boundary, such as a flat rectangular plate 50, which is sized to cover the opening 14, and a supporting load-bearing structure, such as a framework 52. The plate is formed from a material which is resistant to the chemical environment within the chamber 12. A particularly preferred material is stainless steel. The framework 52 is made a material which provides sufficient strength for the door, such as a lower-cost carbon steel, or from a combination of materials which provide the framework with internal structural strength and a cosmetic outer shell. The framework need not be resistant to the environment within the chamber 12 as it is not generally exposed to the sterilizing environment.

The framework 52 is connected to an exterior surface 54 of the plate 50 in such a way as to allow the plate and the framework to expand and contract separately. This allows for differences in the thermal expansion of the two components. In one preferred embodiment, flexible joints, such as straps 56, connect the framework to the plate. The plate 50 is thus able to transmit pressure forces through normal contact with the framework, while the flexible, frictional joints formed by the straps allow differential lateral sliding thermal expansion of the two components so that thermal stresses do not develop.

Figure 7:
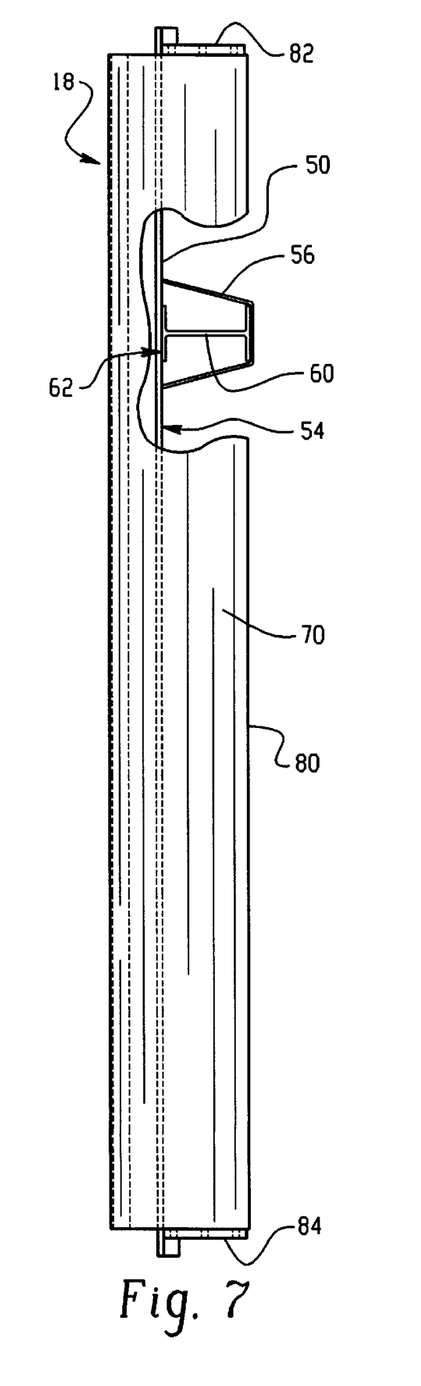
FIG. 7 is an enlarged side view in partial section of the door of FIG. 6.

With reference also to FIG. 7, the framework 52 is constructed so as to provide structural support to the exterior surface 54 of the plate 50. In preferred embodiment, the framework includes an inner structural portion 58 which is formed from a number of parallel-spaced I-beams 60 which are horizontally aligned so that a flat face 62 of each of the I-beams is adjacent to the exterior face 54 of the plate. In a preferred embodiment, the I beams are positioned about 25 centimeters apart, so that for a door of about 2.2 meters in height, seven I beams are used.

A peripheral frame 64, in the shape of an open box connects the I-beams together. The peripheral frame includes upper and lower members 66 and 68, respectively, and two-side members, 70 and 72 respectively, which are connected adjacent peripheral edges to form the box. The peripheral frame is preferably formed from carbon steel for economic purposes. optionally, the exterior of the peripheral frame 64 may be covered with a sheet of stainless steel for cosmetic purposes.

The I-beams are arranged horizontally between the upper and lower members and may be connected to the side members 70 and 72 by any suitable means, such as welding. Alternatively, the peripheral frame is allowed to float on the I beams 60, or is connected to the plate 50.

The straps 56 are preferably formed from a material, such as carbon steel, which withstands the temperatures of the exterior face of the plate. The straps are preferably attached to the plate 50 by welding, although other means of attachment are also contemplated. A central portion of each strap frictionally engages the framework, but is not welded or otherwise immovably connected to it. Of course, other constructions for loosely but nonremovably hanging the plate on the framework are also contemplated. Optionally, the straps are releasably attached so that the framework 52 and the plate may be disconnected for replacement or maintenance of one of the parts.

With particular reference to FIGS. 6 and 7, a number of the straps 56, preferably from two to four straps, attaches each of the I-beams 60 to the plate 50. In the embodiment shown in FIG. 6, four straps are used for the I beams closest to the upper and lower members 66 and 68, while only two straps are used for the remainder of the I beams. Each of the straps passes from the exterior face 54 of the plate, around one of the I-beams, and returns to the exterior face. The straps allow the I beams to expand and contract at different rates to that of the plate, while maintaining a close relationship between the I beams and the plate.

Figure 8:
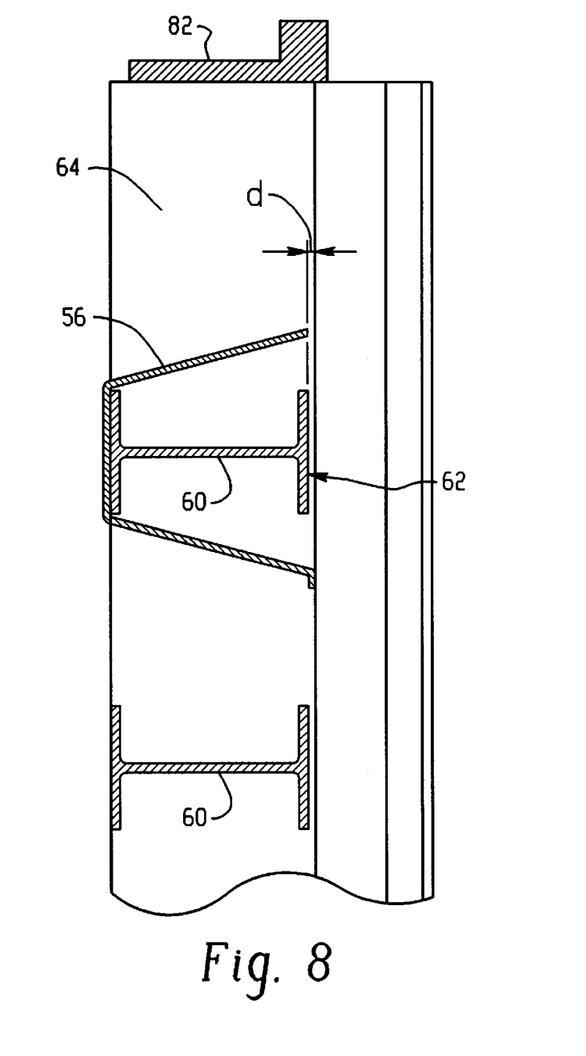
FIG. 8 is an enlarged side cross-sectional view of the door of FIGS. 1 and 2.

In one preferred embodiment, shown in FIG. 8, the straps 56 and the peripheral frame 64 cooperate so as to maintain the inner flat faces 62 of the I beams a spaced distance d, preferably around 0.5 mm or less, from the plate when the door is not subjected to any outward pressure from the chamber. The beams are thus able to slide, relative to the straps and the plate, as they expand and contract. If, however, the pressure inside the chamber causes the plate to bow outwardly by a small amount, the I beams are sufficiently close to the plate to provide a rigid support for the plate and prevent further deformation.

Optionally, there may be a layer of TEFLON™ or other material for promoting smooth sliding movement between the I-beams and the plate 50.

A front cover 80 provides the outer surface of the door furthest from the chamber. The front cover is attached to the peripheral frame 64 to enclose the I beams 60, for cosmetic purposes. The cover also provides an insulation space between the plate 50 and the outer surface of the door.

Figure 9:
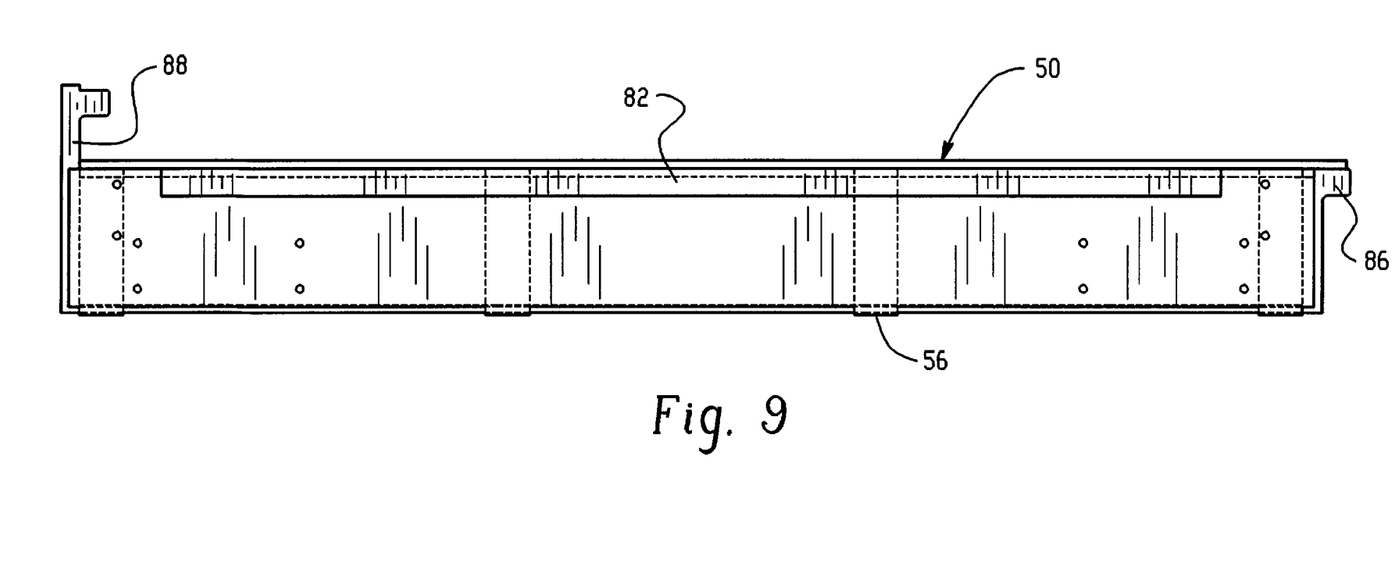
FIG. 9 is an enlarged top view of the door of FIGS. 1 and 2.

With reference once more to FIGS. 3–7, and also to FIG. 9, flanges 82, 84, 86, and 88 extend outwardly from the upper lower, and side members of the frame 66, 68, 70, and 72, respectively. The flanges engage stop plates around the chamber opening when the door 18 is in the closed position. Specifically, flange 86, on the leading edge 26 of the door engages vertical stopping plate 40 while flanges 82, and 84, on the upper and lower members 66 and 68, respectively, engage stopping plates defined by the inner surfaces 34 of the tracks 30 and 36, respectively, and the brackets 39 and 39'. Flange 88, on the trailing edge of the door, is L-shaped and extends beyond the plate 50 to engage a rear face of a backing plate 90 which is connected to the front face 16 of the cabinet around the opening 14. The flanges and stops cooperate to position the door in the closed position and restrain all four sides of the door from bowing under the influence of temperature and pressure changes within the chamber. Preferably, the flanges are formed from stainless steel.

The upper rollers 22 and 24 are rotatably mounted to the upper member 66, while the lower rollers are mounted to the lower member 68.

With reference once more to FIG. 1, a seal 94 is disposed in a channel on the front face 16 of the cabinet around the periphery of the chamber opening 14. The seal is preferably an active seal which is displaced outward from the channel when pressurized steam is pumped into the interior of the seal. Once the door is closed, the seal is activated to seal the door 18 across the opening 14, thereby sealing the chamber opening. Specifically, the seal expands to fill the gap created between the front face 16 of the cabinet and the interior surface of the plate. The door has a certain amount of transverse freedom due to the play provided by the recesses 42, 44 and thus the door may move outwardly a small distance, when the seal is activated, until the flanges fully engage the rearward-facing surfaces of the corresponding stop plates.

During a sterilization cycle, steam or water for producing steam is pumped into the chamber 12 through an inlet 96. A vacuum may be drawn to remove the steam from the items being sterilized or to empty the chamber of air prior to introduction of the steam. When the pressure is reduced inside the chamber 12, the door 18 may move inwardly a small amount, again due to the play provided by the recesses.

Figure 10:
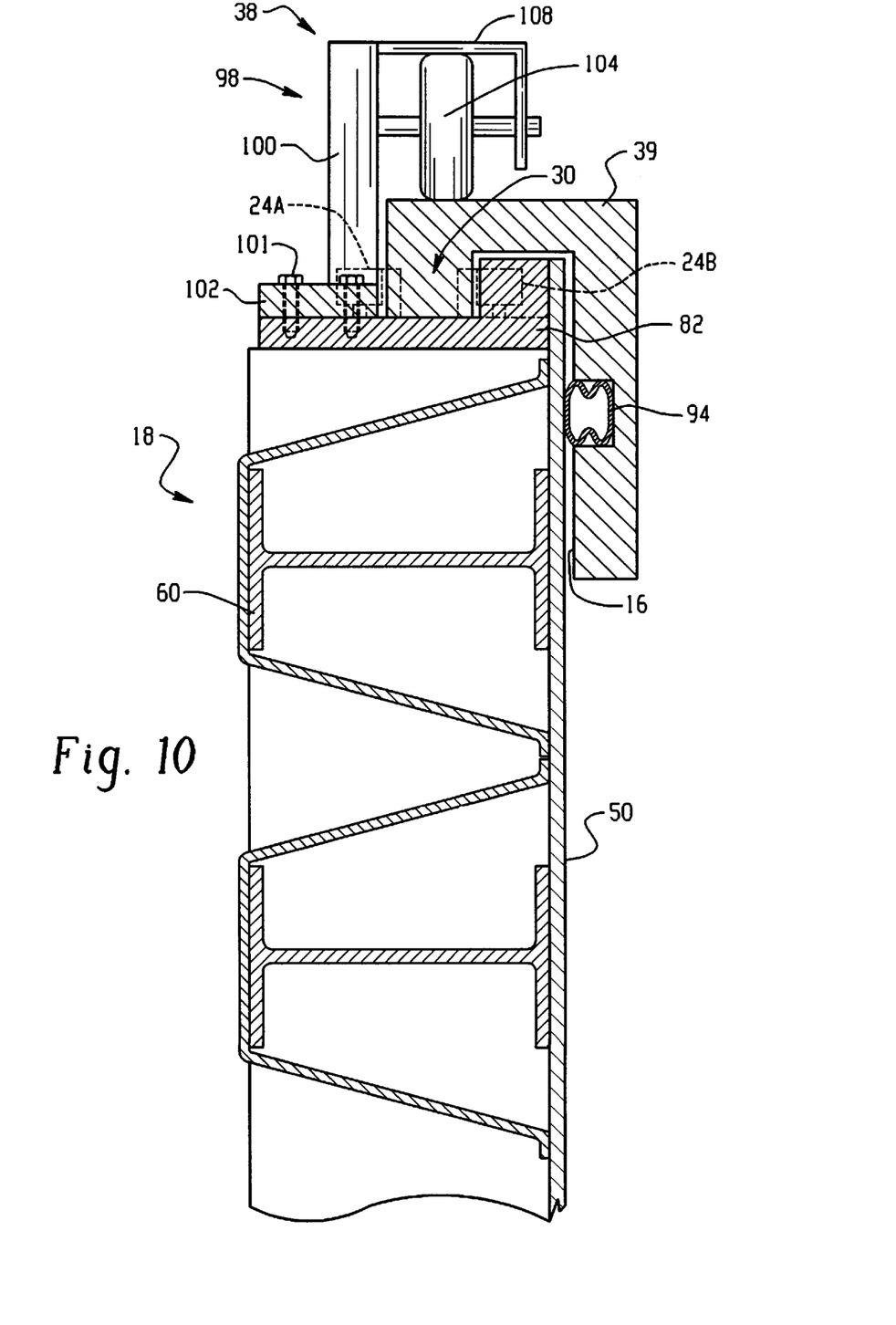
FIG. 10 is a side cross-sectional view of the overhead suspension system of FIG. 1; and, FIG. 11 is a top cross-sectional view of the sterilizer of FIG. 1.

With reference to FIG. 10, a preferred embodiment of the overhead suspension system 38 is shown. The suspension system includes two or more roller assemblies 98, mounted one adjacent the leading edge and one adjacent the trailing edge of the door. Each assembly 98 includes a vertical bracket 100 which is releasably connected to the outside of the door 18 by bolts 101, or other convenient means. Preferably, the bracket 100 is affixed by an outer leg 102 to the top of flange 82. The bracket extends above the track bracket 39 and the track 30. A supporting roller 104 is rotatably supported by the bracket. The supporting roller 104 may be mounted within a housing 108 connected to the bracket 100.

The weight of the door is thus supported on the supporting rollers 104. As the door is opened and closed, the rollers 104 move along the track bracket 39 above the track 30.

Figure 11:
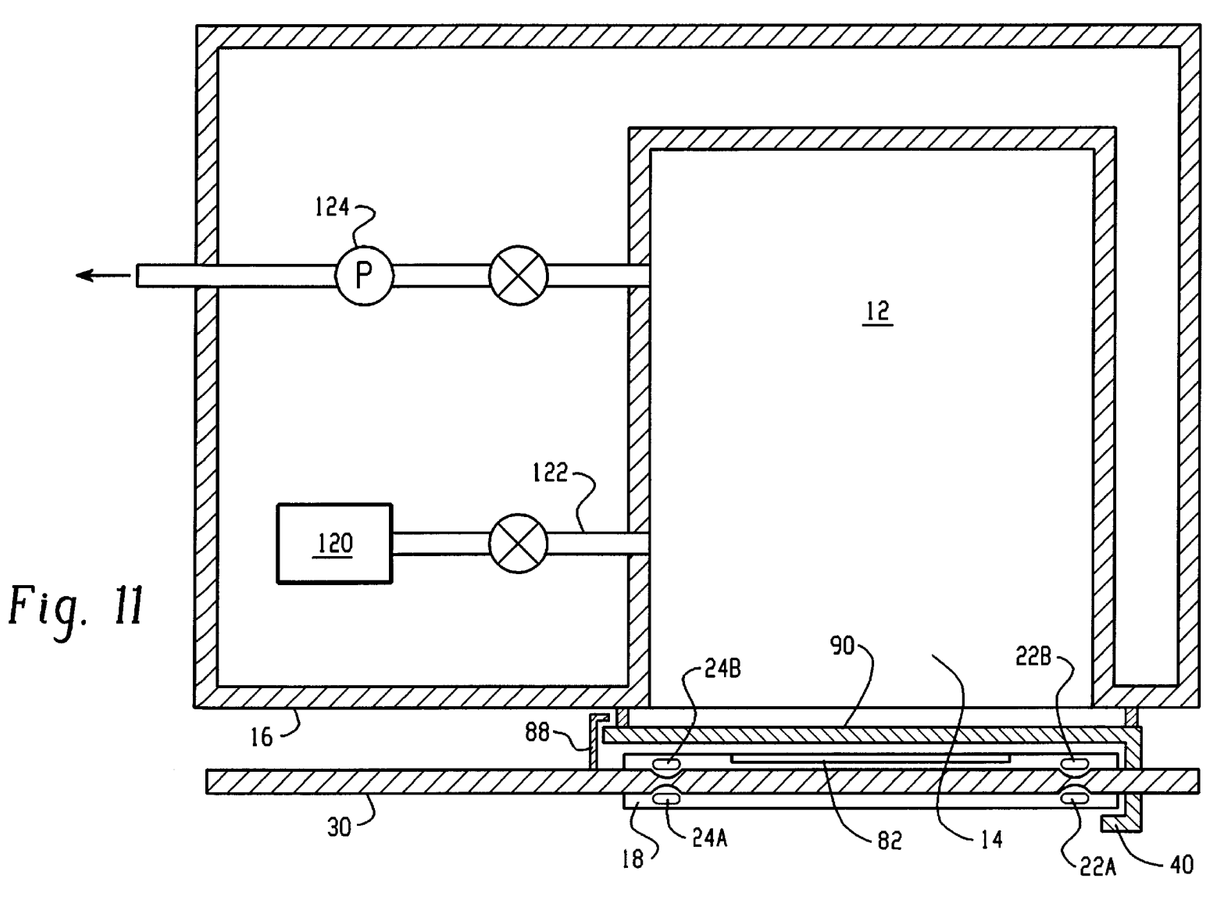

With reference once more to FIG. 1 and reference also to FIG. 11, the sterilizer is operated by first loading items through the opening 14 and into the chamber 12, while the door 18 is in the open position. The door is then moved into the closed position. This may be done manually, by pushing the door so that it moves along the tracks, or by using a motorized system (not shown). Once the door is closed, the seal 94 is activated. This pushes the door outward. Outward movement is limited by the engagement of the flanges 82, 84, 86, 88 with their corresponding stop plates 30, 36, 40, and 90. The inner rollers 22B and 24B enter their corresponding recesses 42B and 44B so that the rollers are not placed under stress by the outward movement of the door. A source of steam, such as a steam generator 120 supplies the chamber with steam through a conduit 122. The added pressure of the steam may cause further outward movement of the door, causing the inner rollers to move slightly further into their respective recesses. The heat of the steam tends to cause the plate 50 to expand. It is able to expand both horizontally and vertically in a plane parallel to the opening without placing buckling stresses on the framework or the rollers.

At the end of the sterilization cycle, a source of vacuum, such as a vacuum pump 124 applies a vacuum to the chamber to draw the steam out of the chamber. The reduced pressure also draws the door plate 50 into closer engagement with the seal which pulls the attached framework and rollers closer to the opening. The outer rollers 22A and 24A enter the corresponding outer recesses 42A and 44A to avoid stresses on the rollers. The depths of the recesses are selected so that the rollers can enter the recesses as the door moves without placing a stress on the rollers.

To convert the door from a left-to-right closing door to a right-to-left closing door, the suspension system 38 is removed and the door flipped 180/ so that the base 52 of the door becomes the top 66. The suspension system is then mounted to the door once more. With the door mounted in the new position, the leading upper rollers 22A and 22B are positioned at the lower left of the door and the leading lower rollers from the base of the door are positioned at the top left of the door which is now the leading edge of the door. The leading side flange 40 is, of course, on the opposite side in a left/right sense. The door is then ready to move toward the left when closing the door.

While the invention has been described with reference to a sliding door, it is to be understood that the invention is also applicable to non-sliding doors, such as hinged doors and to doors which are raised and lowed in a vertical direction rather than an horizontal direction.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the preferred embodiment, the invention is now claimed to be:

1. A walk-in steam microbial decontamination apparatus comprising:

a chamber for receiving items to be microbially decontaminated, the chamber having an opening therein;

a source of steam connected with the chamber;
a door for selectively sealing the opening, the door including:
  a plate sized to cover the opening;
  a framework for providing the door with structural strength to resist buckling of the plate as the pressure or temperature changes within the chamber; and,
  a floating connection which connects the framework to an exterior surface of the plate such that the framework and the plate are free to expand and contract separately in response to a change in temperature, while resisting buckling of the door under the changes in pressure or temperature.

2. The apparatus of claim 1, further including an upper track mounted above the opening and a lower track mounted below the opening, the door moving horizontally between the tracks, and wherein the door further includes: a plurality of rollers rotatably connected to an upper member of the framework for rollingly engaging the upper track.

3. A walk-in steam microbial decontamination apparatus comprising:
  a chamber for receiving items to be microbially decontaminated, the chamber having an opening therein;
  a door for selectively sealing the opening, the door including:
    a plate sized to cover the opening;
    a framework for providing the door with structural strength, the framework including:
      a plurality of spaced beams, and,
      a rectangular peripheral frame which is connected to the beams at ends of the beams; and
    a floating connection which connects the framework to an exterior surface of the plate such that the framework and the plate are free to expand and contract separately in response to a change in temperature.

4. The apparatus of claim 3, wherein the framework is formed from a material which has a different coefficient of thermal expansion from that of the plate.

5. The apparatus of claim 3, wherein the framework includes flanges which extend from sides of the peripheral frame and wherein the chamber includes stop plates disposed adjacent the opening, the flanges engaging the stop plates when the door is in a closed position.

6. A walk-in steam microbial decontamination apparatus comprising:
  a chamber for receiving items to be microbially decontaminated, the chamber having an opening therein;
  a door for selectively sealing the opening, the door including:
    a plate sized to cover the opening;
    a framework for providing the door with structural strength including a plurality of spaced beams; and
    a floating connection which connects the framework to an exterior surface of the plate such that the framework and the plate are free to expand and contract separately in response to a change in temperature, the floating connection including a plurality of straps, the straps being connected to an exterior surface of the plate at a first end of each of the straps and at a second end of each of the straps, the beams being held in loops formed between the ends of each of the straps.

7. A walk-in steam microbial decontamination apparatus comprising:
  a chamber for receiving items to be microbially decontaminated, the chamber having an opening therein;
  a door for selectively sealing the opening, the door including:
    a plate sized to cover the opening;
    a framework for providing the door with structural strength;
    a floating connection which connects the framework to an exterior surface of the plate such that the framework and the plate are free to expand and contract separately in response to a change in temperature; and
    a plurality of rollers rotatably connected to an upper member of the framework, the plurality of rollers including a first set of rollers disposed adjacent a leading edge of the door and a second set of rollers disposed adjacent a trailing edge of the door;
  an upper track mounted above the opening and a lower track mounted below the opening, the door moving horizontally between the tracks, parallel to the opening, the rollers rollingly engaging the upper track, the upper track extending between rollers of the first and second sets to hold the door spaced from the chamber as it moves between open and closed positions, the upper track narrowing in width adjacent the rollers in the closed position to permit the door to move in a direction toward and away from the chamber.

8. A walk-in steam microbial decontamination apparatus comprising:
  a chamber for receiving items to be microbially decontaminated, the chamber having an opening therein, a leading stop plate on the chamber defining a vertically extending U-shaped channel adjacent a leading edge side of the opening and a trailing edge stop plate on the chamber defining a vertically extending projection adjacent a trailing edge side of the opening;
  a horizontal sliding door for selectively sealing the opening, the door including:
    a plate sized to cover the opening;
    a framework for providing the door with structural strength;
    a floating connection which connects the framework to an exterior surface of the plate such that the framework and the plate are free to expand and contract separately in response to a change in temperature;
    a leading edge flange extending vertically along a leading edge of the door, the leading edge flange being received in the stop plate U-shaped channel when the door is in a closed positions
    a trailing edge flange defining a U-shaped channel extending vertically along a trailing edge of the door, the vertically extending projection on the trailing edge side of the opening being received in the U-shaped channel of the trailing edge flange when the door is in the closed position.

9. The apparatus of claim 8, wherein the framework includes:
  a plurality of horizontally extending beams extending between the leading and trailing edge flanges.

10. A door for a steam sterilizer including:
  a single, stainless steel plate sized to cover an entire opening in the sterilizer;
  a structural steel framework for providing the door with structural strength; and,
  a floating connection which connects the framework to an exterior surface of the plate such that the framework and the plate are free to expand and contract separately in response to a change in temperature.

11. The door of claim 10, wherein the floating connection include a plurality of straps.

12. The door of claim 11, wherein the framework includes:
- a plurality of spaced beams; and,
- a rectangular peripheral frame which is connected to the beams at ends of the beams.

13. The door of claim 12, wherein the framework includes flanges which extend from sides of the peripheral frame for engaging stop plates around the opening in the sterilizer when the door is in a closed position.

14. The door of claim 12, further including:
- a first set of rollers rotatably connected to an upper member of the peripheral frame for rollingly engaging an upper track of the sterilizer; and,
- a second set of rollers rotatably connected to a lower member of the peripheral frame for rollingly engaging a lower track of the sterilizer.

15. A door for a sterilizer including:
- a plate sized to cover an opening in the sterilizer;
- a framework for providing the door with structural strength, the framework including a plurality of spaced beams and a peripheral frame which is connected to the beams at ends of the beams; and
- a plurality of straps which connect the framework to an exterior surface of the plate such that the framework and the plate are free to expand and contract separately in response to a change in temperature, the straps being connected to an exterior surface of the plate at a first end of each of the straps and at a second end of each of the straps, the beams being held frictionally in loops formed between the ends of each of the straps.

16. The door of claim 15, wherein at least 3 of the plurality of straps flexibly connect each beam to the exterior surface of the plate.

17. The door of claim 15, wherein the framework is formed from a material which has a different coefficient of thermal expansion from that of the plate.

18. The door of claim 15, wherein:
- the plate is formed from stainless steel; and,
- the framework is formed from carbon steel.

19. A door for a steam cabinet including:
- a plate;
- a framework for providing the door with structural strength, the framework including a plurality of horizontally disposed beams extending between vertical side frame members; and
- a plurality of hangers connected to the plate, the hangers being fixedly connected to the plate and slidably supported on the horizontal beams such that the framework and the plate are free to expand and contract separately in response to a change in temperature.

20. A door for a sterilizer including:
- a plate;
- a framework for providing the door with structural strength,
- a plurality of hangers connected to the plate and slidably supported on the framework such that the framework and the plate are free to expand and contract separately in response to a change in temperature;
- a plurality of rollers which support the framework for horizontal rolling movement;
- a leading edge flange which is received in a U-shaped stop plate when the door is in a closed position; and
- a U-shaped trailing edge flange which receives a projecting rib plate when the door is in the closed position.

21. A method for selectively sealing an opening in a steam cabinet, the method including:
- connecting a framework having peripheral members and a plurality of interior frame members to an exterior surface of a plate with floating connections such that the framework and the plate are free to expand and contract independently in response to changes in temperature, the plate being sized to seal the opening;
- sealing an interior surface of the plate to the cabinet around the opening;
- pressurizing the cabinet with steam; and,
- selectively holding the framework adjacent an exterior surface of the plate to prevent the plate from buckling outward in response to steam pressure in the cabinet.

* * * * *